US012758152B2

(12) United States Patent
Massmann

(10) Patent No.: US 12,758,152 B2
(45) Date of Patent: Oct. 13, 2026

(54) CONTACT QUALITY SYSTEM AND METHOD

(71) Applicant: St. Jude Medical, Cardiology Division, Inc., St. Paul, MN (US)

(72) Inventor: Samuel P. Massmann, Minneapolis, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 1198 days.

(21) Appl. No.: 17/564,691

(22) Filed: Dec. 29, 2021

(65) Prior Publication Data

US 2022/0257196 A1 Aug. 18, 2022

Related U.S. Application Data

(60) Provisional application No. 63/150,818, filed on Feb. 18, 2021.

(51) Int. Cl.
*A61B 5/00* (2006.01)
*A61B 18/00* (2006.01)
(Continued)

(52) U.S. Cl.
CPC .......... *A61B 5/6885* (2013.01); *A61B 5/7221* (2013.01); *A61B 18/1206* (2013.01);
(Continued)

(58) Field of Classification Search
CPC . A61B 5/6885; A61B 5/7221; A61B 18/1206; A61B 18/1492; A61B 18/16; A61B 5/6843; A61B 2018/00577; A61B 2018/00827; A61B 2018/00351; A61B 18/1233; A61B 2018/00666;
(Continued)

(56) References Cited

U.S. PATENT DOCUMENTS

| | | | |
|---|---|---|---|
| 2003/0088185 | A1 | 5/2003 | Prass |
| 2008/0071263 | A1 | 3/2008 | Blaha |

(Continued)

FOREIGN PATENT DOCUMENTS

| | | | |
|---|---|---|---|
| CN | 111050680 A | 4/2020 | |
| EP | 1 902 684 A1 | 3/2008 | |

(Continued)

OTHER PUBLICATIONS

International Search Report and Written Opinion for International Application No. PCT/US2021/065478, mailed Apr. 7, 2022, 19 pages.

(Continued)

*Primary Examiner* — Ronald Hupczey, Jr.
*Assistant Examiner* — Ana Veruska Guerrero
(74) *Attorney, Agent, or Firm* — Billion & Armitage

(57) ABSTRACT

A system includes an ablation generator configured to provide ablation energy to the body via a catheter, and a contact quality monitor configured to provide a quality signal indicative of contact quality associated with the one or more surface body electrodes. The contact quality monitor provides an interrogation signal to the electrodes and receives a sense signal. The contact quality monitor provides a quality signal indicating a low contact quality in response to the sense signal.

13 Claims, 5 Drawing Sheets

(51) Int. Cl.
*A61B 18/12* (2006.01)
*A61B 18/14* (2006.01)
*A61B 18/16* (2006.01)

(52) U.S. Cl.
CPC .......... *A61B 18/1492* (2013.01); *A61B 18/16* (2013.01); *A61B 5/6843* (2013.01); *A61B 2018/00577* (2013.01); *A61B 2018/00827* (2013.01)

(58) Field of Classification Search
CPC ........... A61B 2018/00708; A61B 2018/00875; A61B 2018/00898; A61B 2018/128; A61B 2018/165; A61B 2090/065
See application file for complete search history.

(56) References Cited

U.S. PATENT DOCUMENTS

| | | | | |
|---|---|---|---|---|
| 2009/0198230 | A1* | 8/2009 | Behnke | A61B 18/1233 606/35 |
| 2009/0234352 | A1 | 9/2009 | Behnke et al. | |
| 2009/0234353 | A1* | 9/2009 | McPherson | A61B 18/1233 606/35 |
| 2009/0275827 | A1 | 11/2009 | Aiken et al. | |
| 2011/0204903 | A1 | 8/2011 | Gilbert | |
| 2015/0141978 | A1* | 5/2015 | Subramaniam | A61B 5/0538 606/34 |
| 2015/0359584 | A1* | 12/2015 | Newton | A61B 18/1233 606/34 |
| 2016/0220298 | A1 | 8/2016 | Paul et al. | |
| 2020/0261142 | A1* | 8/2020 | Panescu | A61B 5/01 |
| 2020/0323577 | A1* | 10/2020 | Winstrom | A61B 18/16 |

FOREIGN PATENT DOCUMENTS

| | | | | |
|---|---|---|---|---|
| EP | 1902684 | B1 * | 12/2010 | A61B 18/1233 |
| JP | 2008073827 | A | 4/2008 | |
| JP | 2009183708 | A | 8/2009 | |
| JP | 2019519271 | A | 7/2019 | |

OTHER PUBLICATIONS

"Communication Pursuant to Article 94(3) EPC Received for 21847898.0 mailed on Jun. 25, 2024", 4 Pages.
"International Preliminary Report on Patentability Received mailed on Aug. 31, 2023", 11 Pages.
"Office Action Received for Application No. 2023-549642 mailed on Jun. 18, 2024", 13 Pages.
"Notice of Allowance Mailed on Oct. 1, 2024", 2 Pages.
"Notice of Decision to Grant and Search Report mailed on Jul. 24, 2026", 8 Pages.

* cited by examiner

CONTACT QUALITY SYSTEM AND METHOD

CROSS-REFERENCE TO RELATED APPLICATIONS

This application claims priority to U.S. Provisional Patent Application No. 63/150,818, filed Feb. 18, 2021, which is incorporated by reference herein its entirety.

BACKGROUND

The present disclosure relates to systems and methods of monitoring contact quality of return electrodes, such as body surface electrodes, during an ablation procedure.

Various therapies are used to treat various conditions afflicting the human anatomy. Cardiac arrhythmias, for example are sometimes treated using ablation therapy. When tissue is ablated, or at least subjected to ablative energy generated by an ablation generator and delivered by an ablation catheter, lesions form in the tissue. Electrodes mounted on or in ablation catheters are used to create tissue necrosis in cardiac tissue to correct conditions such as atrial arrhythmia (including, but not limited to, ectopic atrial tachycardia, atrial fibrillation, and atrial flutter). Arrhythmia (i.e., irregular heart rhythm) can create a variety of dangerous conditions including loss of synchronous atrioventricular contractions and stasis of blood flow that can lead to a variety of ailments and even death. It is believed that the primary cause of atrial arrhythmia is stray electrical signals within the left or right atrium of the heart. The ablation catheter imparts ablative energy (e.g., radiofrequency (RF) energy, cryoablation, lasers, chemicals, high-intensity focused ultrasound, etc.) to cardiac tissue to create a lesion in the cardiac tissue. This lesion disrupts undesirable electrical pathways and thereby limits or prevents stray electrical signals that lead to arrhythmias.

RF ablation systems include an RF source and a return. The RF source is generally a small electrode on a tip portion of a catheter, and the return can be one or more return electrodes (e.g., adhesive surface patches) disposed on the body and electrically coupled to a neutral or ground return node. The one or more return electrodes can be attached to the skin of the body using an adhesive or other fastening technique and have greater surface areas than the small electrode on a tip portion of a catheter. A decrease in contact quality can occur if the return electrode loses adhesion to the skin or body during a procedure.

SUMMARY

Some embodiments relate to a system for monitoring contact quality of a first body surface electrode. The system includes a generator configured to provide ablation energy, an electronic control unit (ECU) configured to be in electrical communication with the first body surface electrode and the generator, and a circuit connecting the first body surface electrode to the ECU. The ECU is configured to send an interrogation signal through the circuit to the first body surface electrode and receive a sense signal through the circuit in response to the interrogation signal. The ECU determines the contact quality of the first body surface electrode by processing the sense signal.

In some embodiments, the interrogation signal is provided at a first frequency if the ablation energy is being provided and at a second frequency if the ablation energy is not being provided. In some embodiments, the first body surface electrode comprises a first conductive portion and a second conductive portion, and the first conductive portion is separated from the second conductive portion by a gap. The interrogation signal can be provided across the gap, and the sense signal can have a voltage corresponding to an impedance across the gap.

Some embodiments relate to a system that includes a second body surface electrode and a variable impedance circuit coupled in series with at least one of the first body surface electrode and the second body surface electrode. The system also includes a first current sensor configured to sense a first current level associated with the ablation energy provided by the generator through the first body surface electrode, and a second current sensor configured to sense a second current level associated with the ablation energy provided by the generator through the second body surface electrode. The circuit is coupled to the first current sensor and the second current sensor. The circuit provides a control signal to the variable impedance circuit to balance the first current level through the first body surface electrode and the second current level through the second body surface electrode.

In some embodiments, the first frequency is lower than the second frequency, the first frequency being between 10 kilohertz (kHz) and 20 kHz and the second frequency being between 20 kHz and 200 kHz. In some embodiments, the circuit provides a quality signal in response to the sense signal being in a first relationship with a threshold and dynamically adjusts the threshold in response to a current level associated with the ablation energy provided by the generator through the first body surface electrode.

Some embodiments relate to a method of determining contact quality of a first body surface electrode attached to a body. The method includes providing an interrogation signal to the first body surface electrode. The interrogation signal is provided at a frequency. The frequency is determined in response to whether ablation energy is or is not being provided to the body. The method also includes receiving a sense signal from the first body surface electrode in response to the interrogation signal and processing the sense signal to determine the contact quality.

In some embodiments, a method can balance current through a first and second body surface electrode. The method includes sensing a first current level associated with the ablation energy through the first body surface electrode, sensing a second current level associated with the ablation energy provided through the second body surface electrode, and balancing current through the first body surface electrode and through the second body surface electrode in response to the first current level and the second current level.

BRIEF DESCRIPTION OF THE DRAWINGS

The disclosure will become more fully understood from the following detailed description, taken in conjunction with the accompanying figures, wherein like reference numerals refer to like elements, in which.

DETAILED DESCRIPTION

The present disclosure relates to a dynamically configurable contact quality monitor system and method. The present disclosure also relates to a contact quality monitor or control system and method that actively balances current through two or more return electrodes. In some embodiments, the systems and methods are configured to adjust the frequency of interrogation signals provided to the return electrode to improve contact quality measurements and avoid interference. Higher frequency interrogation signals are used during non-treatment (e.g., non-ablation) periods to obtain a more reliable, consistent reading of contact quality in some embodiments. Lower frequency interrogation signals are used during treatment (e.g., ablation) periods to gain frequency separation, avoid interference and have continued monitoring during treatment periods in some embodiments. Advantageously, the contact quality systems and methods of some embodiments do not solely rely upon comparing a sense signal derived from interrogation signal to a fixed threshold to determine low contact quality (e.g., a 30-40% reduction in adhered patch area) of the return electrode according to some embodiments.

According to some embodiments, the contact quality systems and methods issue contact quality alarms or trips using the immediate RF current levels through the return electrode or electrodes. Advantageously, the contact quality systems and methods monitor individual current levels through two or more return electrodes and/or actively balance the current among the return electrodes. Details of the various examples of the present disclosure are described below with specific reference to the figures.

Figure 1:
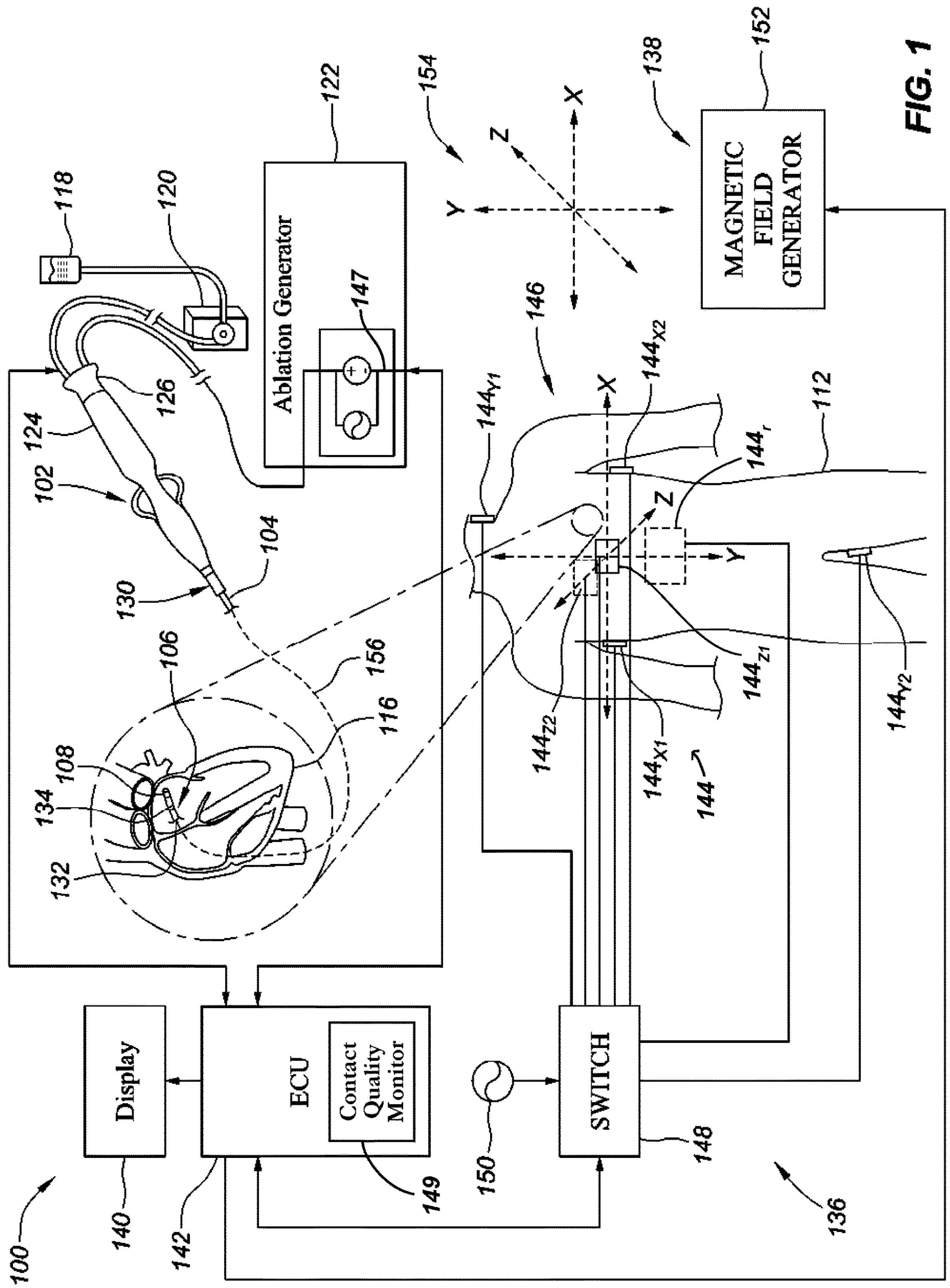
FIG. 1 is a schematic drawing of a system for navigating and operating a medical device within a body according to some embodiments.

Referring to FIG. 1, one example of a system 100 for navigating and operating a medical device within a body 112 comprises a catheter 102, such as an ablation catheter, that is shown schematically entering a heart (e.g., tissue 116) that has been exploded away from the body 112. In some embodiments, catheter 102 can be from the TactiCath™ family of contact force ablation catheters, such as the TactiCath™ Contact Force Ablation Catheter, Sensor Enabled™ from Abbott Laboratories. It should be understood, however, that the system 100 can find application in connection with a wide variety of medical devices used within the body 112 for diagnosis or treatment. Further, it should be understood that the system 100 can be used to navigate medical devices used in the diagnosis or treatment of portions of the body 112 other than tissue 116 (e.g., cardiac tissue). Further description of the systems and components are contained in U.S. patent application Ser. No. 13/839,963 filed on 15 Mar. 2013, now U.S. Pat. No. 9,693,820, which is hereby incorporated by reference in its entirety as though fully set forth herein.

The catheter 102 can include a handle 124, a cable connector or interface 126 at a proximal end of the handle 124, and a shaft 104 (also referred to herein as a catheter shaft). The shaft 104 can include a proximal end 130, and a distal end 132. A tip portion 106 can be located at the distal end 132. The handle 124 provides a location for the physician to hold the catheter 102 and can further provide means for steering or guiding the shaft 104 within the body 112. For example, the handle 124 can include means to change the length of one or more pull wires extending through the catheter 102 from the handle 124 to the distal end 132 of shaft 104. The construction of the handle 124 can vary.

The shaft 104 can be made from conventional materials such as polyurethane and can define one or more lumens configured to house and/or transport electrical conductors 156, fluids, or surgical tools. The shaft 104 can be introduced into a blood vessel or other structure within the body 112 through a conventional introducer. The shaft 104 can then be steered or guided through the body 112 to a desired location such as the tissue 116 using guide wires or pull wires or other means known in the art including remote control guidance systems. The shaft 104 can also permit transport, delivery, and/or removal of fluids (including irrigation fluids and bodily fluids), medicines, and/or surgical tools or instruments. It should be noted that any number of methods can be used to introduce the shaft 104 to areas within the body 112. This can include introducers, sheaths, guide sheaths, guide members, guide wires, or other similar devices. For ease of discussion, the term introducer will be used throughout.

In some examples, the system 100 can include a positioning system, a display 140, and an electronic control unit (ECU) 142. The ECU 142 can include, but is not limited to, a central processing unit (CPU), graphics processing unit (GPU), microprocessor, application specific integrated circuit (ASIC), a field programmable gate array (FPGA), complementary metal-oxide-semiconductor (CMOS), or the like. In some examples, the ECU can include memory, such as random-access memory (RAM), read-only memory (ROM), programmable read-only memory (PROM), erasable programmable read-only memory (EPROM), and electrically erasable programmable read-only memory (EEPROM), dynamic random-access memory (DRAM), static random-access memory (SRAM), Flash memory, or the like. The ECU 142 is a processor-based circuit in some embodiments.

The positioning system is a hybrid electric-field-based (impedance-based) and magnetic-field-based system including an electric-field-based positioning system 136 and a magnetic-field-based positioning system 138 in some embodiments. For example, the positioning system can be an EnSite Precision™ Cardiac Mapping System from Abbott Laboratories. The positioning system is provided to determine the position and orientation of the catheter 102, the tip portion 106, and similar devices within the body 112. For instance, the location or orientation of the tip portion 106 can be based on a fiducial or location of one or more electrodes of the tip portion 106, such as locational electrodes 134. In some examples, the locational electrodes 134 can include ring electrodes as shown in the example of FIG. 1. The system 136 operates based upon the principle that when low amplitude electrical signals are passed through the thorax, the body 112 acts as a voltage divider (or potentiometer or rheostat) such that the electrical potential or field strength measured at one or more electrodes, such as locational electrodes 134, on the catheter 102 can be used to determine the position of the catheter 102 relative to a pair of external patch electrodes using Ohm's law and the relative location of a reference electrode (e.g., in the coronary sinus).

In the configuration shown in FIG. 1, the electric-field-based positioning system 136 further includes three pairs of body surface electrodes 144. The three pairs of the body surface electrodes 144 are patch electrodes which are provided to generate electrical signals used in determining the position of the catheter 102 within a three-dimensional coordinate system 146 in some embodiments. The body surface electrodes 144 can also be used to generate electrophysiology (EP) data (e.g., electrophysiological signals) regarding the tissue 116. To create axes-specific electric fields within body 112, the body surface electrodes 144 are placed on opposed surfaces of the body 112 (e.g., chest and back, left and right sides of the thorax, and neck and leg) and form generally orthogonal X, Y, and Z axes. A reference electrode is typically placed near the stomach, provides a reference value and acts as the origin of the coordinate system 146 for the navigation system.

In accordance with this exemplary electric-field-based positioning system 136 as depicted in FIG. 1, the body surface electrodes 144 include right side patch $\mathbf{144}_{X1}$, left side patch $\mathbf{144}_{X2}$, neck patch $\mathbf{144}_{Y1}$, leg patch $\mathbf{144}_{Y2}$, chest patch $\mathbf{144}_{Z1}$, and back patch $\mathbf{144}_{Z2}$; and each body surface electrode 144 is connected to a switch 148 (e.g., a multiplex switch) and a signal generator 150. The body surface electrodes $\mathbf{144}_{X1}$, $\mathbf{144}_{X2}$ are placed along a first (X) axis; the body surface electrodes $\mathbf{144}_{Y1}$, $\mathbf{144}_{Y2}$ are placed along a second (Y) axis, and the body surface electrodes $\mathbf{144}_{Z1}$, $\mathbf{144}_{Z2}$ are placed along a third (Z) axis. Sinusoidal currents are driven through each pair of body surface electrodes 144, and voltage measurements for one or more position sensors (e.g., locational electrodes 134) associated with the catheter 102 are obtained. The measured voltages are a function of the distance of the position sensors from the patch electrodes. The measured voltages are compared to the potential at the reference electrode and a position of the position sensors within the coordinate system 146 of the navigation system is determined.

In some embodiments, body surface electrodes 144 include at least one return electrode **144*r* for providing a return path to a return node 147 of the ablation generator 122 during ablation procedures. In some embodiments, the body surface electrodes 144 are provided in the Ensite™ NavX™ Surface Electrode Kit from Abbott Laboratories. In some embodiments, the return electrode 144*r* is one or more large surface area patches provided on a lower back of the body 112. In some embodiments, one or more of the body surface electrodes 144 discussed above can be configured for use as the return electrode 144*r*** for ablation procedures. Exemplary configurations and uses of patch electrodes or body surface electrodes are discussed in U.S. Patent Application Publication No. 2017/0100055 incorporated herein by reference.

In some embodiments, the ECU 142 includes a contact quality monitor 149. In some embodiments, the ECU 142 is integrated into the ablation generator 122. Contact quality monitor 149 can be a standalone unit, part of switch 148, or other component of system 100 in some embodiments. The contact quality monitor 149 can be part of or integrated with one or more of the generator 122, the switch 148 and the ECU 142. Contact quality monitor 149 sends an interrogation signal across the return electrode **144*r* and processes a sense signal associated with the interrogation signal to determine impedance of the return electrode 144*r* through the skin/body and hence, the contact quality. The contact quality monitor 149 provides warnings and automatic tripping of the system 100 to shut off provision of ablation energy if the contact quality is insufficient in some embodiments. In some embodiments, the contact quality monitor 149 makes continuous measurements of current through each of multiple return electrodes 144*r* and adjusts the series impedance of each return path to actively balance the current through the return electrodes 144*r*. The operation of the contact quality monitor 149 is described in more detail below with respect to FIGS. 2-5** and can be used with any type of return electrodes.

The magnetic-field-based positioning system 138 in this example employs magnetic fields to detect the position and orientation of the catheter 102 within the body 112. In such a system, a magnetic field generator 152 can be employed having three orthogonally arranged coils (not shown) to create a magnetic field within the body 112 and to control the strength, orientation, and frequency of the field. The magnetic field generator 152 can be located above or below the patient (e.g., under a patient table) or in another appropriate location. Magnetic fields are generated by the coils and current or voltage measurements for one or more position sensors associated with the catheter 102 are obtained. The measured currents or voltages are proportional to the distance of the sensors from the coils, thereby allowing determination of a position of the sensors within a coordinate system 154 of system 138.

As the catheter 102 moves within the body 112, and within the electric field generated by the electric-field-based positioning system 136, the voltage readings from the locational electrodes 134 change, thereby indicating the location of catheter 102 within the electric field and within the coordinate system 146 established by the system 136. The locational electrodes 134 can be adapted to communicate position signals to the ECU 142.

The catheter 102 can be configured to deliver treatment as well as geometric modeling or electrophysiological mapping. In some examples, the catheter 102 can include at least one electrode 108 configured to detect electrophysiological signals from the tissue 116 or to provide energy for ablating the tissue 116. In an example, the at least one electrode 108 can be communicatively coupled to the ablation generator 122 for delivery of electrical signals adapted to provide the ablation energy to the at least one electrode 108. The ablation generator 122 can be an Ampere™ Generator from Abbott Laboratories and provides a sinusoidal electrical signal at 485 kilohertz (kHz) in some embodiments. Other types, frequencies, and forms of RF signals can be provided from the ablation generator 122. In some embodiments, at least one electrode 108 is an electrode assembly that may be used for a variety of diagnostic and therapeutic purposes including, for example and without limitation, cardiac mapping and/or ablation (e.g., RF ablation or Irreversible Electroporation (IRE ablation)/Pulsed Field Ablation (PFA)). The ablation generator 122 can be configured for bipolar PFA, which uses a train of bipolar and biphasic pulses of high voltage and short duration to create tissue modification without significant heating. For example, the electrode assembly may be configured as a bipolar electrode assembly for use in bipolar-based electroporation therapy. Specifically, a pair of electrodes are individually electrically coupled to an IRE generator (e.g., ablation generator 122 configured to be an IRE generator) and are configured to be selectively energized with opposite polarities to generate a potential and corresponding electric field there between for IRE therapy. That is, one of electrodes is configured to function as a cathode, and the other is configured to function as an anode. In some embodiments, the at least one electrode 108 may configured as a monopolar electrode assembly and use a patch electrode (as a return or indifferent electrode) (e.g., the return electrode **144*r***). The electrodes can provide ablation energy for IRE treatment by delivering electric current as a pulsed electric field (i.e., PFA) in the form of ultrashort pulses (2-5 microsecond (μs) pulse width and 20-40 μs pulse period) grouped in bursts of 100-1000 pulses.

In some embodiments, monopolar IRE ablation energy is provided at voltages of 2.5 kV resulting in peak pulse currents up to 100 A.

In some examples, the catheter 102 can be optionally connected to a fluid source 118 for delivering a biocompatible irrigation fluid such as saline through a pump 120. The pump 120 can include a fixed rate roller pump or variable volume syringe pump with a gravity feed supply from fluid source 118 as shown. The connector or interface 126 provides mechanical, fluid, and electrical connections for conduits or cables extending from the pump 120 and the ablation generator 122. The catheter 102 can also include other conventional components not illustrated herein such as a temperature sensor, additional electrodes, and corresponding conductors or leads. In some embodiments, the tip portion 106 includes tip electrodes associated with a grid catheter or basket catheter.

The ECU 142 provides a device for controlling the operation of various components of the system 100, including the catheter 102, the ablation generator 122, and magnetic field generator 152 of the magnetic-field-based positioning system 138. The ECU 142 can also provide a device for determining electrophysiology characteristics (e.g., signals) of the tissue 116, the position and orientation of the catheter 102 relative to tissue 116 and the body 112, controlling the ablation of the tissue 116, or any combination thereof. The ECU 142 also provides a device for generating display signals used to control the display 140.

The display 140 is provided to convey information to a physician to assist in diagnosis and treatment. The display 140 can comprise one or more conventional computer monitors or other display devices. The display 140 can present a graphical user interface (GUI) to the physician. The GUI can include a variety of information including, for example, contact quality information, warnings, or alarms, an image of the geometry of the tissue 116, electrophysiology data (e.g., maps of signals from the electrode 108) associated with the tissue 116, graphs illustrating voltage levels over time for various locational electrodes 134, and images of the catheter 102 and other medical devices and related information indicative of the position of the catheter 102 and other devices relative to the tissue 116.

Figure 2:
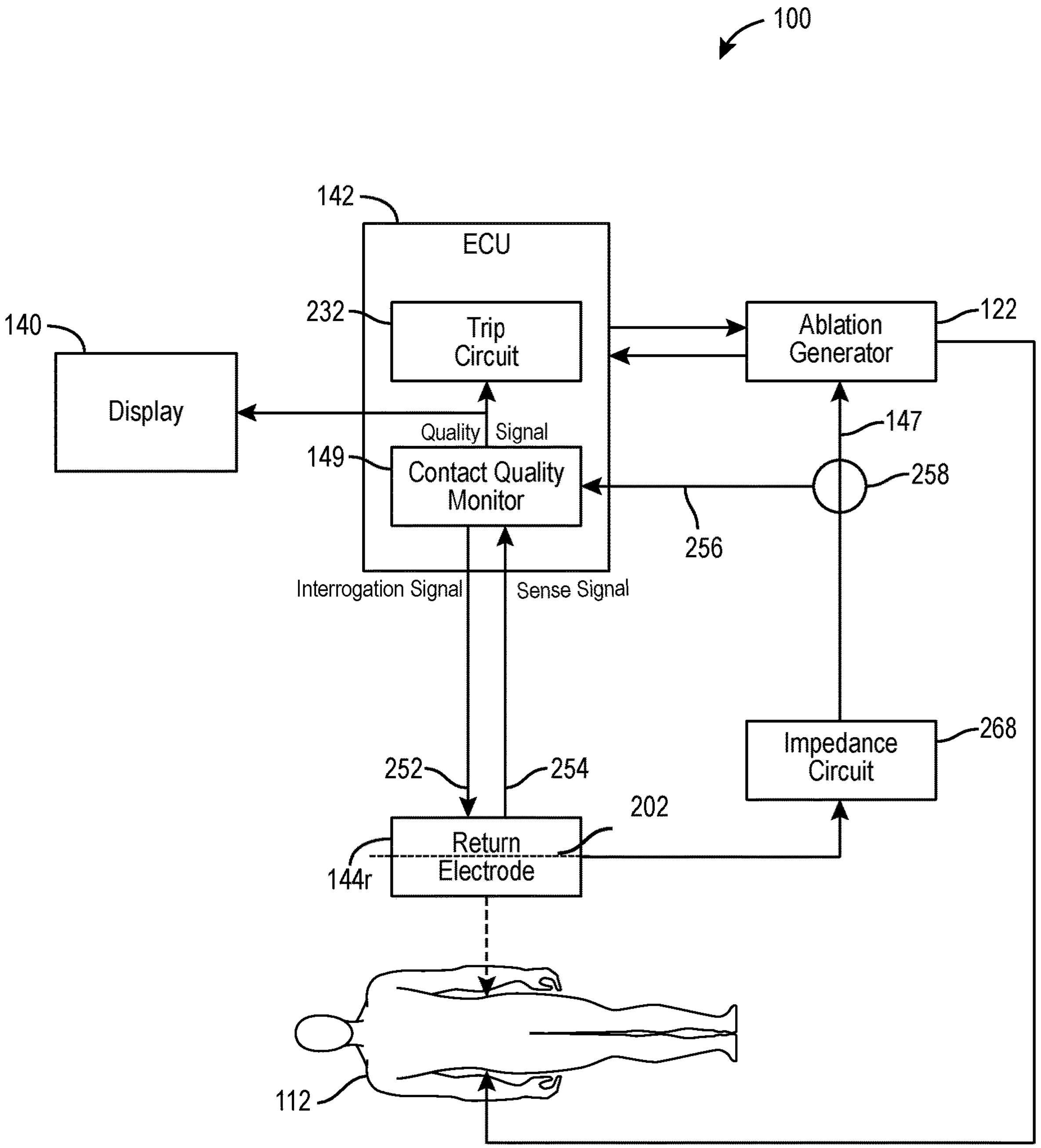
FIG. 2 is a general block diagram of an electronic control unit (ECU) for the system illustrated in FIG. 1 according to some embodiments.

Referring to FIG. 2, the ECU 142 includes the contact quality monitor 149 and a trip circuit 232. The ECU 142 is coupled to the display 140 and the ablation generator 122. The contact quality monitor 149 is coupled to one or more body surface electrodes 144 to provide a treatment to body 112 (e.g., human or animal). At least one return electrode **144*r* is provided in a return path from the body 112 to the return node 147 of the ablation generator 122** in some embodiments.

The return electrode **144*r* can be a single return electrode embodied as a patch in some embodiments. The return electrode 144*r* can be two or more return electrodes embodied as two or more patches in some embodiments. In some embodiments, the return electrode 144*r* can be of various shapes, such as, square, rectangular, circular, trapezoidal, etc. In some embodiments, the return electrode 144*r* includes conductive portions electrically separated by a split or gap so that contact quality can be determined based upon impedance associated with the split as explained below. The return electrode 144*r* can be an adhesive, conductive structure that is applied to the skin on the lower back or other parts of the body 112. The return electrode 144*r* can be a surface body electrode as described in U.S. Patent Application Publication No. 2017/0100055 incorporated herein by reference and provides a good electrical contact to the skin of the patient's body 112. Various conductive materials and layers can be used in the return electrode 144*r***, such as, silver carbon film, metal films, conductive adhesives or gels, a conductive foam sponge material, barrier layers, etc. Other methods of transferring electrical energy such as capacitive coupling of a conductive element to the patient's skin may also be practiced.

The contact quality monitor 149 is also coupled to a current transformer 258 and a variable impedance circuit 268. In some embodiments, the contact quality monitor 149 is a monitor or control circuit that performs at least one of the following operations: 1) providing an interrogation signal at a first frequency in a range between 20 kHz and 200 kHz in a first period when ablation is not being performed and at a second frequency in a range between 10 kHz and 20 kHz in a second period when ablation is being performed; and 2) providing a signal indicating low contact quality in response to sense signal being in a relationship with a threshold, the threshold being set in response to a current level used during ablation.

In some embodiments, the contact quality monitor 149 is a circuit (e.g., processor-based circuit) including a conductor or lead 252 that provides an interrogation signal to the return electrode **144*r*. In some embodiments, the return electrode 144*r* is a single patch with a gap or a split 202 electrically dividing the conductive medium of the return electrode 144*r*. The interrogation signal is provided at a conductor, lead, or output 252 and travels across the split 202 via the contact between the skin and the return electrode 144*r*. A conductor, lead, or input 254 provides the sense signal from the return electrode 144*r* to the contact quality monitor 149. Output 252 and input 254 provide an interface for providing and receiving the interrogation signals and the sense signals and can include more than one conductor. The sense signal is derived from the interrogation signal and is representative of the impedance across the split 202 and hence the contact quality. In some embodiments, the interrogation signal is a constant current signal provided across the split 202, and the sense signal is a voltage measurement across the split 202 representative of impedance across the split 202. The sense signal is compared to a threshold to determine if the contact quality is sufficient for the procedure. In some embodiments, the contact quality monitor 149 provides a quality signal to the trip circuit 232 as well as other parts of the ECU 142. In some examples, the ECU 142 can provide alarms, warnings, or other contact information for display on the display 140** in response to the quality signal.

The trip circuit 232 shuts down, disables, or prevents the provision of the ablation energy by the ablation generator 122 when the quality signal indicates that the contact quality is not sufficient (e.g., a 30-40 percent reduction in adhered patch area). The trip circuit 232 includes a switch that isolates the ablation generator 122 from the body 112 in some embodiments. In some embodiments, the trip circuit 232 is part of the contact quality monitor 149 and provides an interrupt or flag to the ECU 142 in the event of insufficient contact quality.

In some embodiments, the interrogation signal is provided in a lower frequency range (e.g., 10-20 kHz) during ablation to avoid interference with the higher frequency signals from the ablation generator 122. This separation in frequency also allows, with standard electronic components, a low-impedance path for the return of energy to the return node 147 and the higher impedance path for the interrogation signal in some embodiments. Additionally, capacitive components of the impedance of the body 112 are more pronounced at lower frequencies, which can result in additional inconsistencies in the measurements of contact quality. Accordingly, the interrogation signal is provided at a higher frequency in a higher frequency range (e.g., 20-200 kHz) when ablation is not provided to provide a more consistent, accurate measurement of impedance and contact quality.

The current concentration $I_{con}$ is found by taking the total patch current $I_{patch}$ divided by the adhered patch area $A_{effective}$ (assuming there is uniform distribution of current through the effective patch area) ($I_{con}=I_{patch}/A_{effective}$). Therefore, if the patch current is low, there is a lower minimum adhered area required for proper current concentration.

In some embodiments, the quality signal indicates insufficient contact quality when impedance is higher than a threshold representing impedance associated with insufficient conatc quality. The threshold is not a fixed threshold and is adjusted according to the current or power level received at the return node 147 in some embodiments. The threshold is decreased when the current level is higher because a higher level of contact quality (lower impedance) may be needed during higher current ablation procedures in some embodiments. A lower level of contact quality is tolerable during lower current procedures in some embodiments. In some embodiments, the contact quality monitor 149 uses an algorithm to continuously adjust the threshold for contact quality (adhered patch area) based on the amount of current through the return electrode 144*r*.

The current transformer 258 provides a power sense signal or current level signal to the contact quality monitor 149 via a lead 256. The current transformer 258 can be any device for sensing power or current in the conductor associated with the return node 147 in some embodiments. The peak current level used during the procedure can be used to adjust the threshold in some embodiments. In some embodiments, the peak current level in a period of time is used. In some embodiments, real time current level is used to adjust the threshold. In some embodiments, the current level is provided by ECU 142 based upon system configuration or user input. In some embodiments, the threshold is also adjusted based upon whether the higher frequency interrogation signal is provided when ablation is not being performed or whether the lower frequency interrogation signal is provided when ablation is performed (e.g., a threshold specific for each of the higher and lower frequency interrogation signals). In some embodiments, a magnitude of the threshold is inversely related to the current level associated with the ablation energy provided by the ablation generator 122 through the return electrode 144*r*.

In some embodiments, the threshold represents a threshold impedance for low contact quality. The sense signal is a voltage signal that represents impedance (e.g., the higher the sense signal the higher the impedance) in some embodiments. When the sense signal is above the threshold, a low contact quality signal is provided. The low contact quality signal can be used to provide warnings or trip the system 10. Conversely, a signal representing sufficient contact quality can be provided when the sense signal is below the threshold. The threshold can be selected or adjusted for a particular type of return electrode 144*r*, the number of return electrodes 144*r*, the location of the return electrode 144*r* on the body 112, or the type of procedure. The particular type of return electrode 144*r*, the number of return electrodes 144*r*, and the location of the return electrode 144*r* can be sensed or input as data by a user.

In some embodiments, the threshold is fixed and represents current concentration. The actual current concentration $I_{con}$ is compared to the threshold where actual current concentration $I_{con}$ is calculated using the sense signal (representing $A_{effective}$) and the current level from the current transformer 258 ($I_{patch}$)($I_{con}=I_{patch}/A_{effective}$). Using current concentration $I_{con}$ or a dynamic threshold is advantageous, because the number of situations in which the output is inappropriately disabled is reduced.

The contact quality signal is also provided to the ECU 142 for audible or visual warning of a low contact quality. The warning can be provided in accordance with the threshold in some embodiments. A warning or caution can also be provided if a change in impedance becomes higher even though the threshold is not reached. A quickly increasing impedance can indicate that adjustment of the return electrode 144*r* may be required in some embodiments. The display 140 can also provide an analog indication of contact quality based upon the contact quality signal or the sense signal.

In some embodiments, the contact quality monitor 149 adjusts the impedance of the impedance circuit 268 between the return electrode 144*r* and return node 147. The impedance circuit 268 includes one or more of active devices, resistors, capacitors or inductors for adjusting impedance via switched paths, active control or other control technique.

The ECU 142 and contact quality monitor 149 are implemented as a circuit including one or more of a general purpose processor, a specific purpose processor, memory, application specific integrated circuits (ASICs), field programmable gate arrays (FPGAs), groups of processing components, interface, isolation, and filter components, analog and digital support circuits or other suitable electronic processing components. The memory is one or more storage devices (e.g., RAM, ROM, flash memory, hard disk storage) for storing data and computer code for completing and facilitating the various -processes, layers, and modules described in the present disclosure. The memory may be or include volatile memory or non-volatile memory and may include database components, object code components, script components, or any other type of information structure for supporting the various activities and information structures of the inventive concepts disclosed herein. The memory is communicably connected to the processor and includes computer code or instruction modules for executing one or more processes described herein. The memory includes various circuits, software engines, and/or modules that cause the one or more processors to execute the systems and methods described herein.

Figure 3:
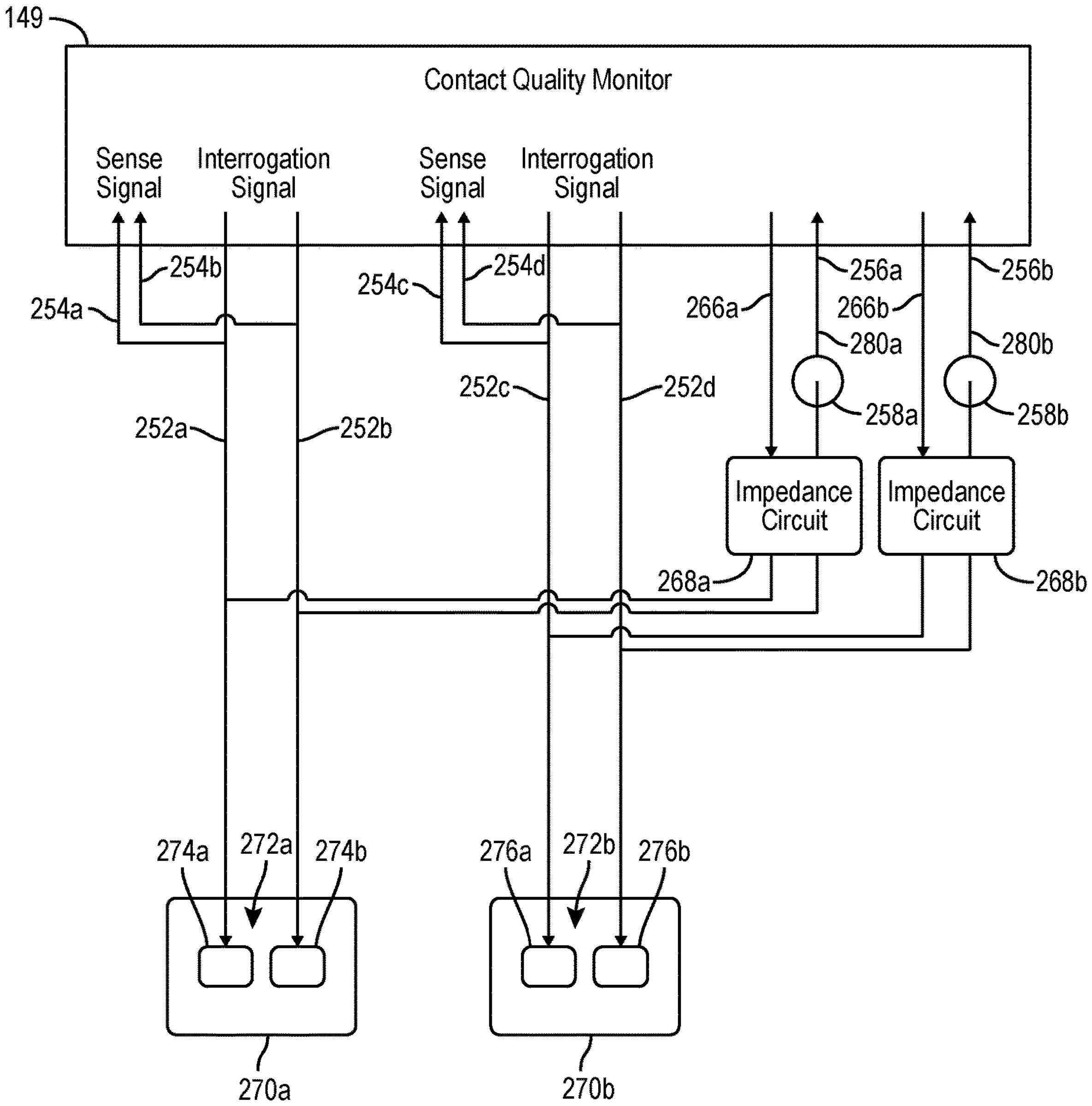
FIG. 3 is a general block diagram of the contact quality monitor illustrated in FIG. 2 coupled to two return electrodes according to some embodiments.

With reference to FIG. 3, the contact quality monitor 149 is coupled to the return electrode 144*r* (FIG. 2) embodied as two or more return electrodes 270*a* and 270*b*. Any number of return electrodes 144*r* can be used with the contact quality monitor 149 where each return electrode 144*r* is associated with a channel for a respective interrogation signals, sense signals, sensed current levels, impedance adjustment, etc. Return electrodes 270*a* and 270*b* are placed asymmetrically on the body. The placement can result in a lower impedance path through the body from the tip portion 106 (FIG. 1) to one of the return electrodes 270*a* and 270*b* over another of the return electrodes 270*a* and 270*b*. Due to the lower impedance path, one of the return electrodes 270*a* and 270*b* can receive more return energy than the other of the return electrodes 270*a* and 270*b*. This can create an imbalance in which one return electrode of the return electrodes 270*a* and 270*b* passes more current than the other return electrode of the return electrodes 270*a* and 270*b*. This can be undesirous in a high current mode where even distribution of return current is desired.

Return electrode 270*a* includes two conductive portions, 274*a* and 274*b*, separated by a gap or split 272*a*, and return electrode 270*b* includes two conductive portions, 276*a* and 276*b*, separated by a gap or a split 272*b*. A lead 252*a* is coupled to portion 274*a*, and a lead 252*b* is coupled to portion 274*b*. A lead 252*c* is coupled to portion 276*a*, and a lead 252*d* is coupled to portion 276*b*. A sense input 254*a* is coupled to portion 274*a*, and a sense input 254*b* is coupled to portion 274*b*. A sense input 254*c* is coupled to portion 276*a*, and a sense input 254*d* is coupled to portion 276*b*. Leads 252*a-b* are the signal and return nodes for the interrogation signal for return electrode 270*a*, and leads 252*c-d* are the signal and return nodes for the interrogation signal for return electrode 270*b*. Sense inputs 254*a-b* are for the sense signal for return electrode 270*a*, and sense inputs 254*c-d* are for the sense signal for return electrode 270*b*.

The sense signal across the sense inputs 254*a* and 254*b* is compared to a threshold to determine contact quality of the return electrode 270*a*. The threshold is dynamically adjusted based upon a current level sensed by the current transformer 258*a*. The sense signal across the sense inputs 254*c* and 254*d* is compared to a threshold to determine contact quality of the return electrode 270*b*. The sense signals at inputs 254*a-b* and 254*c-d* are voltage measurements of the interrogation signals across splits 272*a-b* in some embodiments. The threshold is dynamically adjusted based upon a current level sensed by the current transformer 258*b*. A contact quality signal can be provided for each of return electrodes 270*a* and 270*b* as well as a composite contact quality signal for both return electrodes 270*a* and 270*b*.

In some embodiment, the return paths for return electrodes 270*a* and 270*b* include respective impedance circuits 268*a* and 268*b* coupled to respective portions 274*a-b* and 276*a-b*. The impedance circuits 268*a* and 268*b* can be adjusted to balance return current between the return electrodes 270*a* and 270*b*. Leads 266*a-b* provide an interface to the contact quality monitor 149 and can be used to control impedance in the impedance circuits 268*a-b* in response to current level signals from current transformers 258*a* and 258*b* indicating current in the return electrodes 270*a* and 270*b*. If return electrode 270*a* is receiving more return current than return electrode 270*b*, the impedance of impedance circuit 268*a* in the return path of return electrode 270*a* can be increased or the impedance of impedance circuit 268*b* in the return path of electrode 270*b* can be decreased to balance the return current between return electrodes 270*a* and 270*b*.

Current transformers 258*a* and 258*b* provide current level signals via leads 256*a-b* indicative of the current in each return path. Leads 256*a* and 256*b* provide an interface to the contact quality monitor 149. A comparison of the current levels sensed by current transformers 258*a-b* is used to determine the amount of impedance adjustment. Advantageously, each return electrode 270*a* and 270*b* is connected to return node 147 (FIG. 1) through impedance circuits 268*a-b*. Impedance circuits 268*a-b* are coupled to portions 274*a-b* and 276*a-b*, respectively, and a respective single conductor 280*a-b* is provided through each of current transformers 258*a-b* to return node 147 (FIG. 1). Impedance circuits 268*a-b* are printed circuit boards (PCBs) with an adjustable LC (inductor-capacitor) resonant trap circuit and variable resistance R in some embodiments. In some embodiments, for components not adjustable through digital control, an array of relays is used to switch components that are connected in the return path to adjust the impedance. In some embodiments, return electrodes 270*a* and 270*b* can be any number of electrodes including three, four or more electrodes, each associated with a path or channel having a respective impedance circuit, current sensor, and interface for a sense signal and an interrogation signal.

Figure 4:
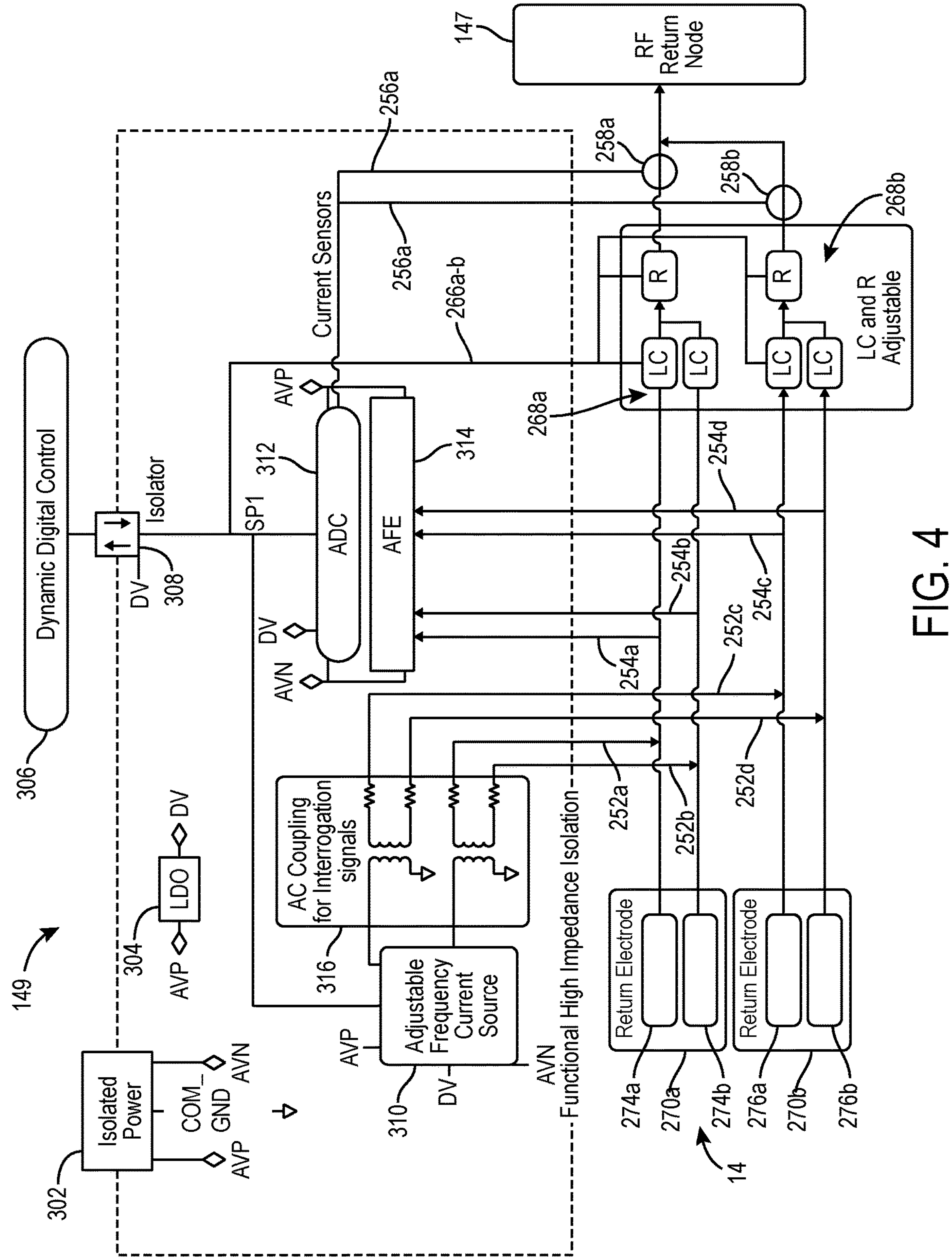
FIG. 4 is a more detailed block diagram of the contact quality monitor illustrated in FIG. 3 according to some embodiments-.

With reference to FIG. 4, the contact quality monitor 149 includes an isolated power circuit 302, a power converter 304, dynamic digital control circuit 306, an isolator 308, an adjustable frequency current source 310, an analog to digital converter 312, an analog front end circuit 314, and an isolation circuit 316 in some embodiments. In some embodiments, the contact quality monitor 149 is coupled to return electrodes 270*a* and 270*b*. Dynamic digital control circuit 306 is a processor or other circuit configured to provide the operations described herein with regard to contact quality monitoring and control. The analog to digital converter 312 provides digital data to the dynamic digital control circuit 306 representing sense signals from inputs 254*a-d* and current level signals from current transformers 258*a-b*.

Impedance circuits 268*a* and 268*b* are coupled in the return path of return electrodes 270*a* and 270*b*, respectively. Advantageously, each return electrode 270*a* and 270*b* is connected to return node 147 through a respective impedance circuit 268*a-b*. Dynamic digital control circuit 306 controls impedance circuits 268*a-b* via digital control signals on leads 266*a-b* in some embodiments. Dynamic digital control circuit 306 provides the signals on the leads 266*a-b* for load balancing in response to the current level sense signals provided via leads 256*a-b* and analog to digital converter 312. Analog front end circuit 314 provides frequency conversion, filtering, conditioning and other interface functions before the sense signals are converted into digital data.

Dynamic digital control circuit 306 provides the interrogation signals at different frequencies depending upon whether ablation energy is provided (e.g., whether return node 147 is receiving current associated with signals from the ablation generator 122 (FIG. 1) in some embodiments). In some embodiments, dynamic digital control circuit 306 receives a signal or data from ECU 142 (FIG. 1) indicating that ablation energy is provided so that an appropriate frequency can be selected for the interrogation signal. The frequency may be chosen based upon the frequency of the electric signals for ablation to avoid interference, harmonic frequencies, etc. The ability to select a frequency for the interrogation signal that does not interfere with other equipment or components within system 100 is advantageous. For example, positioning systems or mapping systems can provide hundreds of impedance-measuring signals with frequencies between 8 and 9 kHz and 16 and 22 kHz, and the interrogation signal can be provided outside of these bands to avoid interference.

In some embodiments, the interrogation signals are provided via an alternating current coupling circuit such as isolation circuit 316. The adjustable frequency current source 310 is controlled digitally and drives an interrogation signal across the return electrodes 270*a* and 270*b* or a single patch electrode in some embodiments. The adjustable frequency current source 310 is a constant current source, and the interrogation signals are provided at a current between at 10-100 microamperes (uA) root mean square (RMS) in some embodiments. The resulting voltage across the return electrodes 270*a* and 270*b* is provided via inputs 254*a-d* through the analog front end circuit 314 as the sense signals to the analog to digital converter 312 for receipt by the dynamic digital control circuit 306. The analog front end circuit 314 is tuned to achieve proper performance at all usable frequencies (approximately 10 kHz-100 kHz) in some embodiments.

Power converter 304 is a drop out regulator in some embodiments. Dynamic digital control is a processor-based circuit, field programmable gate array, application specific circuit (ASIC), microcontroller, or combination thereof in some embodiments. An isolation barrier provides high impedance isolation from return electrodes 270*a* and 270*b* and return node 147. Isolation circuit 316 is a transformer-based circuit in some embodiments.

Although the example of FIG. 4 is shown with two return electrodes 270*a* and 270*b*, the contact quality monitor 149 can be configured for more than two return electrodes 270*a* and 270*b* by adding a channel for each additional return electrode. In some embodiments, the contact quality monitor 149 can be configured for a single return electrode 270*a* by removing the channel associated with the return electrode 270*b*.

Figure 5:
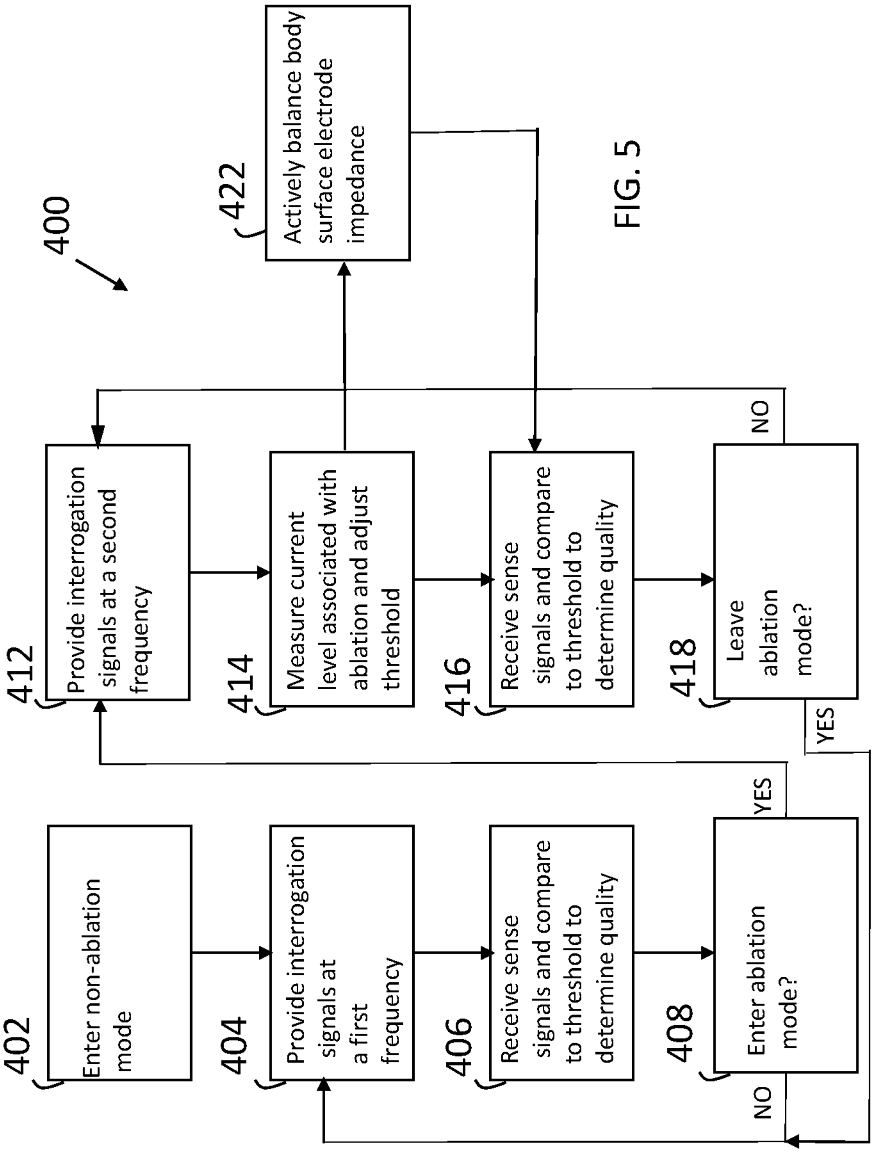
FIG. 5 is a flow diagram showing exemplary operations of the system illustrated in FIG. 1 according to some embodiments.

With reference to FIGS. 1 and 5, the system 100 and contact quality monitor 149 operate according to flow 400 in some embodiments. At an operation 402, system 100 is in a non-ablation mode where ablation energy is not being provided to the body 112 in some embodiments. The non-ablation mode can include a quiet mode in which the ablation generator 122 is powered on or not completely off and the system 100 is not providing ablation energy. In some embodiments, the ablation generator 122 can provide a low amplitude signal (e.g., at 485 kHz) for measurement purposes in the non-ablation mode.

At an operation 404, the contact quality monitor 149 provides interrogation signals at a first frequency. The first frequency is in a frequency range between 20 and 200 kHz in some embodiments. A higher frequency interrogation signal provides more accurate impedance readings and can be used during a non-ablation mode because the higher frequency, higher amplitude ablation signals are not present and therefore, do not interfere with the higher frequency interrogation signal. In some embodiments, the first frequency has an upper limit of approximately 100 kHz to avoid interference with signals from the ablation generator 122. In some embodiments, the first frequency is above 100 kHz or above 200 kHz signal and is chosen to avoid interference with signals from the ablation generator 122 (e.g., measurement signals such as the 485 kHz measurement signal). In some embodiments, the first frequency is provided at a frequency between 20-200 kHz that is selected to obtain accurate and stable patch impedance readings. The first frequency can be selected in accordance with system parameters and design criteria such as avoidance of signal interference from other signals in the system 100 and electrical characteristics (e.g., capacitance, inductance, and resistance of the return electrode 144*r* (FIG. 1) and filters), etc.

At an operation 406, the contact quality monitor 149 receives sense signals and compares the sense signals to a threshold to determine contact quality. The contact quality is used to provide alarms or trip operation of the system 100. The threshold can represent impedance and be adjusted lower in accordance with the amount of ablation energy provided during ablation treatment (e.g., a lower threshold for higher amounts of ablation energy).

At an operation 408, the contact quality monitor 149 returns to operation 404 if the ablation mode is not entered. The ablation mode is a period where ablation energy is provided to the body 112 in some embodiments. Entry into the ablation mode can be determined from a signal from ECU 142, a user input, or the presence of current associated with ablation energy at return electrode 144*r*.

If the ablation mode is entered, the contact quality monitor 149 advances to an operation 412. At operation 412, the contact quality monitor 149 provides provide interrogation signals at a second frequency lower than the first frequency. In some embodiments, the second frequency is between 5 and 50 kHz (e.g., 10-20 kHz). In some embodiments, the second frequency is 12 kHz. As the interrogation signal frequency gets closer to the frequency (e.g., 485 kHz) of the ablation signal provided by the ablation generator 122, more noise or interference is present. In some embodiments, the second frequency is at least one logarithmic decade (order of magnitude) away from the frequency of the ablation signal (e.g., an approximately 50 kHz upper limit when the frequency of the ablation signal is approximately 500 kHz) so that RF noise can be effectively filtered out. The second frequency is high enough so that the impedance measurements are not inconsistent due to body/patch/skin capacitive effects showing up in the measurement. A lower frequency limit for the second frequency can be dependent on characteristics of the return electrode 144*r* (FIG. 1) and the body 112.

At an operation 412, the contact quality monitor 149 measures the current level associated with the ablation energy and adjusts the threshold in accordance with the current level. At an operation 422, the contact quality monitor 149 performs active balancing of body surface electrodes impedance in response to current levels through the return electrodes 144*r* (e.g., measured at operation 414). Operation 422 is used if two or more return electrodes 144*r* are used in system 100. Operation 422 is optional in some embodiments.

After operation 414 or 422, the contact quality monitor 149 receives sense signals and compares the sense signals to a threshold to determine contact quality in an operation 416. The threshold can be dynamically adjusted as discussed above. After operation 416 and at an operation 418, the contact quality monitor 149 returns to operation 404 if system 100 has not left the ablation mode. If the non-ablation mode is entered, the contact quality monitor 149 advances to operation 404. Operations 414 and 412 can be performed simultaneously with other operations in flow 400. After operations 406 and 416, ablation operations can be stopped if contact quality is insufficient.

Although embodiments are described above with respect to RF ablation treatment, RF ablation treatment is not disclosed in a limiting fashion. For example, the contact quality monitor 149 can be used with an IRE ablation treatment without departing from the scope of the claims. For example, a monopolar IRE system with two or more return electrodes 144*r* could use the current balancing technique of the contact quality monitor 149. In another example, a monopolar IRE system used with one or more return electrodes 144*r* could use the dynamic threshold technique of the contact quality monitor 149. Further, the contact quality monitor 149 can be used with other treatments and procedures that use one or more return electrodes 144*r* without departing from the scope of the claims. Although embodiments are described above with respect to cardiac treatment, contact quality monitor 149 can be used with systems designed to treat other organs. Although embodiments are described above with respect to catheter ablation treatment, contact quality monitor 149 can be used with non-catheter ablation systems.

It is to be understood that embodiments of the methods according to the inventive concepts disclosed herein may include one or more of the steps described herein. Further, such steps may be carried out in any desired order and two or more of the steps may be carried out simultaneously with one another. Two or more of the steps disclosed herein may be combined in a single step, and in some embodiments, one or more of the steps may be carried out as two or more sub-steps. Further, other steps or sub-steps may be carried out in addition to, or as substitutes to one or more of the steps disclosed herein. Although processors and non-transitory computer media is disclosed, the circuits for performing the described operations can take other forms.

From the above description, it is clear that the inventive concepts disclosed herein are well adapted to carry out the objects and to attain the advantages mentioned herein as well as those inherent in the inventive concepts disclosed herein. While presently preferred embodiments of the inventive concepts disclosed herein have been described for purposes of this disclosure, it will be understood that numerous changes may be made which will readily suggest themselves to those skilled in the art and which are accomplished within the broad scope and coverage of the inventive concepts disclosed and claimed herein.

What is claimed is:

1. A system for monitoring contact quality of a first body surface electrode, the system comprising:

a generator configured to provide ablation energy;

an electronic control unit (ECU) configured to be in electrical communication with the first body surface electrode and the generator;

a circuit connecting the first body surface electrode to the ECU;

wherein the ECU is configured to send an interrogation signal through the circuit to the first body surface electrode and receive a sense signal through the circuit in response to the interrogation signal;

wherein the ECU determines the contact quality of the first body surface electrode by processing the sense signal and provides a low contact quality signal when the sense signal is higher than a threshold; and wherein the circuit is configured to dynamically adjust the threshold in response to a current level associated with the ablation energy provided by the generator through the first body surface electrode.

2. The system of claim 1, wherein the threshold is adjusted lower when the current level associated with the ablation energy provided by the generator through the first body surface electrode is increased.

3. The system of claim 1, wherein the circuit comprises a current transformer disposed between a return node of the generator and the first body surface electrode, wherein the current level is determined using a current signal from the current transformer.

4. The system of claim 1, wherein the circuit comprises an analog-to-digital converter for receiving the sense signal.

5. A method of determining contact quality of a first body surface electrode, the method comprising:

providing ablation energy from an ablation generator to a body during a time interval, the ablation generator comprising a return node coupled to the first body surface electrode;

providing a single interrogation signal to the first body surface electrode, the interrogation signal having a frequency related to whether the ablation energy is being provided to the body from the ablation generator, wherein the interrogation signal is provided at a first frequency if the ablation energy is being provided to the body and at a second frequency if the ablation energy is not being provided to the body;

receiving a sense signal from the first body surface electrode in response to the interrogation signal, wherein the sense signal is related to an impedance between the body and the first body surface electrode; and processing the sense signal to determine the contact quality;

wherein the sense signal is processed by comparing the sense signal to a threshold, and the method further comprises providing a low contact quality signal when the sense signal is above the threshold, and wherein a magnitude of the threshold is inversely related to the current level associated with the ablation energy provided by the ablation generator through the first body surface electrode.

6. The method of claim 5, wherein the first frequency is lower than the second frequency.

7. The method of claim 6, wherein the first frequency is between 10 kHz and 20 kHz and the second frequency is between 20 kHz and 200 kHz.

8. The method of claim 5, wherein the first body surface electrode comprises a first conductive portion and a second conductive portion, wherein the first conductive portion is separated from the second conductive portion by a gap, and wherein the interrogation signal is provided across the gap and the sense signal has a voltage corresponding to the impedance.

9. The method of claim 5, further comprising:

sensing a first current level associated with the ablation energy provided by the ablation generator through the first body surface electrode;

sensing a second current level associated with the ablation energy provided through a second body surface electrode; and balancing current through the first body surface electrode and through the second body surface electrode in response to a difference between the first current level and the second current level.

10. The method of claim 9, wherein balancing the current uses an adjustable impedance circuit.

11. The method of claim 5, further comprising activating a trip circuit to shut down, disable, or prevent the provision of the ablation energy by the ablation generator in response to the low contact quality signal.

12. The method of claim 5, wherein the ablation energy is delivered as a pulsed electric field.

13. A method of determining contact quality of a first body surface electrode, the method comprising:

providing ablation energy from an ablation generator to a body during a time interval, the ablation generator comprising a return node coupled to the first body surface electrode;

providing an interrogation signal to the first body surface electrode, the interrogation signal having a frequency related to whether the ablation energy is being provided to the body from the ablation generator;

receiving a sense signal from the first body surface electrode in response to the interrogation signal, wherein the sense signal is related to an impedance between the body and the first body surface electrode; and processing the sense signal to determine the contact quality, wherein the sense signal is processed by comparing the sense signal to a threshold, and the method further comprises providing a low contact quality signal when the sense signal is above the threshold; and adjusting the threshold in response to a current level associated with the ablation energy provided by the ablation generator through the first body surface electrode.

* * * * *